US011484636B2

(12) United States Patent
Bergman et al.

(10) Patent No.: US 11,484,636 B2
(45) Date of Patent: Nov. 1, 2022

(54) MEDICAL DEVICE HAVING INTEGRATED STERILE WORK PLATFORM

(71) Applicant: Fresenius Medical Care Holdings, Inc., Waltham, MA (US)

(72) Inventors: Eric Bergman, Newton, MA (US); David Yuds, Hudson, NH (US); Jonathan Leclerc, Northborough, MA (US); Mary Vasseur Finn, Ayer, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 419 days.

(21) Appl. No.: 16/850,152

(22) Filed: Apr. 16, 2020

(65) Prior Publication Data

US 2021/0322658 A1    Oct. 21, 2021

(51) Int. Cl.
*A61M 1/16*        (2006.01)
*A61L 2/10*        (2006.01)
(Continued)

(52) U.S. Cl.
CPC ............. *A61M 1/168* (2013.01); *A61L 2/10* (2013.01); *A61L 2/26* (2013.01); *A61M 1/1621* (2014.02);
(Continued)

(58) Field of Classification Search
CPC ...... A61M 1/168; A61M 1/1621; A61M 1/28; A61M 2209/10; A61M 1/14; A61L 2/10; A61L 2/26; A61L 2202/11; A61L 2202/24
See application file for complete search history.

(56) References Cited

U.S. PATENT DOCUMENTS 4,412,834 A * 11/1983 Kulin ................... A61M 1/285
                                                    604/905
4,475,900 A * 10/1984 Popovich ................. A61L 2/26
                                                    604/905
(Continued)

FOREIGN PATENT DOCUMENTS

WO     2016/205051     12/2016

OTHER PUBLICATIONS

International Search Report and Written Opinion in International Appln. No PCT/US2021/027067, dated Jul. 28, 2021, 12 pages.
(Continued)

*Primary Examiner* — David A Vanore
(74) *Attorney, Agent, or Firm* — Fish & Richardson P.C.

(57) ABSTRACT

A medical device, such as a dialysis machine, may have multiple features and components that must be checked and attached prior to a treatment, and operators often lay tubing and other components on a surface after removing them from packaging. The system described herein provides a sterile work platform that is integrated with the medical device. In an example, the platform may be moveably coupled to the medical device. In a first position, the platform is positioned within or against the medical device, and, in a second position, the platform is extended from the medical device and disposed in a horizontal position. After the platform is extended to the second position, a surface of the platform is sterile and suitable to maintain aseptic technique for tubing and components placed on the platform. An information screen may be integrated into the platform and that provides information to an operator.

19 Claims, 9 Drawing Sheets

(51) Int. Cl.
*A61L 2/26* (2006.01)
*A61M 1/28* (2006.01)

(52) U.S. Cl.
CPC ........ *A61L 2202/11* (2013.01); *A61L 2202/24* (2013.01); *A61M 1/28* (2013.01)

(56) References Cited

U.S. PATENT DOCUMENTS

| | | | | |
|---|---|---|---|---|
| 7,208,092 | B2* | 4/2007 | Micheli | A61M 1/166 210/257.2 |
| D607,564 | S | 1/2010 | Crnkovich et al. | |
| 8,197,087 | B2* | 6/2012 | Sobue | A61M 1/28 362/249.02 |
| 9,186,449 | B2 | 11/2015 | Singh et al. | |
| 9,550,005 | B2* | 1/2017 | Lin | A61M 25/002 |
| 11,071,853 | B2* | 7/2021 | Ball | G02B 6/0096 |
| 2014/0276373 | A1* | 9/2014 | Minkus | A61M 1/1674 604/28 |
| 2016/0055303 | A1 | 2/2016 | Keller | |
| 2016/0091984 | A1 | 3/2016 | Tanenbaum et al. | |
| 2017/0014564 | A1 | 1/2017 | Heinemann | |
| 2017/0087290 | A1* | 3/2017 | Medina | G16H 40/63 |
| 2017/0168688 | A1* | 6/2017 | Yuds | A61M 1/3403 |
| 2017/0172695 | A1 | 6/2017 | Daniel | |
| 2019/0381232 | A1* | 12/2019 | Crnkovich | A61M 1/3643 |
| 2019/0388600 | A1* | 12/2019 | Yuds | G01F 9/001 |
| 2020/0197589 | A1 | 6/2020 | Peesapati | A61M 1/1672 |
| 2020/0294392 | A1 | 9/2020 | Peesapati | G16H 40/67 |
| 2020/0310553 | A1* | 10/2020 | Crnkovich | G06F 3/0202 |
| 2020/0368418 | A1* | 11/2020 | Yuds | A61M 1/3607 |
| 2020/0405934 | A1* | 12/2020 | Yuds | C02F 1/685 |
| 2021/0038165 | A1* | 2/2021 | Bergman | A61B 5/0205 |
| 2021/0322658 | A1* | 10/2021 | Bergman | A61M 1/14 |

OTHER PUBLICATIONS

U.S. Appl. No. 16/367,411, Crnkovich, filed Mar. 28, 2019.
2008T Hemodialysis Machine Operator's Manual for software version 2.10 or later, Fresenius Medical Care.

* cited by examiner

MEDICAL DEVICE HAVING INTEGRATED STERILE WORK PLATFORM

TECHNICAL FIELD

This application relates generally to medical devices and, in particular, dialysis machines.

BACKGROUND

Medical devices, such as dialysis machines, are known for use in the treatment of renal disease. The two principal dialysis methods are hemodialysis (HD) and peritoneal dialysis (PD). During hemodialysis, the patient's blood is passed through a dialyzer of a hemodialysis machine while also passing dialysate through the dialyzer. A semi-permeable membrane in the dialyzer separates the blood from the dialysate within the dialyzer and allows diffusion and osmosis exchanges to take place between the dialysate and the blood stream. Before the blood is returned to the body, air bubbles are removed from the blood to inhibit embolisms. The process of removing air is typically accomplished through use of a venous drip chamber, which is located downstream of the blood outlet of a dialyzer and upstream of the venous blood return of the patient.

During peritoneal dialysis, the patient's peritoneal cavity is periodically infused with dialysate, or dialysis solution. The membranous lining of the patient's peritoneum acts as a natural semi-permeable membrane that allows diffusion and osmosis exchanges to take place between the solution and the blood stream. Automated peritoneal dialysis machines, also called PD cyclers, are designed to control the entire peritoneal dialysis process so that it can be performed at home, usually overnight, without clinical staff in attendance. Both HD and PD machines may include displays with touch screens or other user interfaces that display information of a dialysis treatment and/or enable an operator or patient to interact with the machine.

Because a dialysis system involves multiple features and components that must be checked and attached prior to a treatment, operators often lay tubing and other components on a surface after removing them from packaging. This action may potentially break aseptic technique (a control measure critical to preventing infections). Further, nurses and patient care technicians often drape tubing over their gown-covered arms and skillfully control the tubing from slipping while looking it over as they place it on the machine, and/or they may use a rolling cart/tray or other work surface to manage supplies. These surfaces, however, may not be sterile or adequately disinfected. Additionally, home dialysis patients, where space is especially limited, can sometimes use any available and potentially dirty/dusty/non-sterile surface such as chairs, coffee tables, and end tables (with non-dialysis items on them), and/or their own makeshift platforms.

Accordingly, it would be desirable to provide a system that addresses the above-noted concerns and other issues.

SUMMARY

According to the system described herein, a medical device system includes a medical device and a platform moveably coupled to the medical device. In a first position, the platform is positioned within or against the medical device, and, in a second position, the platform is extended from the medical device and disposed in a horizontal position. After the platform is extended to the second position, a surface of the platform is sterile. The medical device may be a dialysis machine in a dialysis system.

In some implementations, the system may further include a sterilization device coupled to the medical device that sterilizes the surface of the platform. The sterilization device may be disposed in an internal port of the medical device. The sterilization device may sterilize the surface of the platform after the platform is retracted into the internal port of the medical device. The sterilization device may include an ultraviolet (UV) light sterilization device that exposes the surface of the platform to UV light and/or the sterilization device may include at least one disinfectant roller that engages the surface of the platform. The system may further comprise a sterile material assembly that applies a sterile material to the surface of the platform when the platform is moved from the first position to the second position. The sterile material assembly may include a dispenser that dispenses the sterile material and a guide that guides the sterile material onto the surface of the platform.

In some implementations, in the first position, the platform may be, or function as, a door to the medical device, and the platform may be made of a transparent material. In the second position, the platform may include an information screen that is formed into the surface of the platform and that presents information when the platform is in the second position. The information screen may be a digital screen and may be formed in the platform using electrically controlled opacity. The system may further comprise a sensor that senses when the platform is in the first position and the second position, and the information screen may be removed when the platform is in the first position. The system may further comprise a control unit of the medical device that controls display of the information screen on the platform. The system may further comprise a communication unit that receives information from a remote source that is displayed on the information screen of the platform.

BRIEF DESCRIPTION OF THE DRAWINGS

Embodiments and features of the system described herein are explained with reference to the several figures of the drawings, which are briefly described as follows.

DETAILED DESCRIPTION

Figure 1:
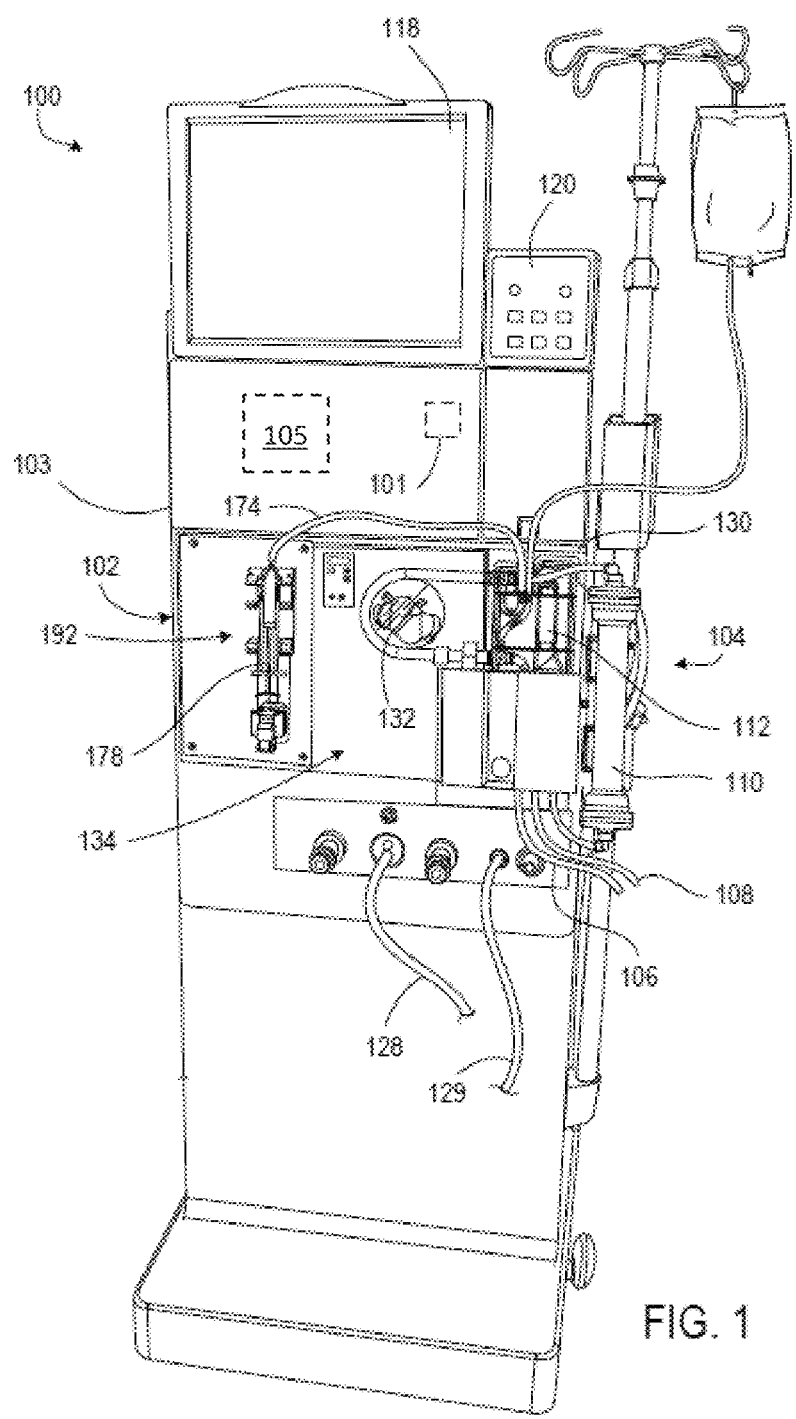
FIG. 1 illustrates an exemplary embodiment of a dialysis machine, specifically a hemodialysis machine, configured in accordance with the present disclosure.

FIG. 1 shows a hemodialysis system 100. The hemodialysis system 100 includes a hemodialysis machine 102 connected to a disposable blood component set 104 that partially forms a blood circuit. During hemodialysis treatment, an operator connects arterial and venous patient lines 106, 108 of the blood component set 104 to a patient. The blood component set 104 may include an air management device 112 that may include, for example, a venous drip chamber.

The blood component set 104 is secured to a module 130 attached to the front of the hemodialysis machine 102. The module 130 includes the blood pump 132 capable of circulating blood through the blood circuit. The module 130 also includes various other instruments capable of monitoring the blood flowing through the blood circuit. The module 130 includes a door that when closed, as shown in FIG. 1, cooperates with the front face of the module 130 to form a compartment that is sized and shaped to receive the blood component set 104.

The blood pump 132 is part of a blood pump module 134. The blood pump module 134 includes a display window, a start/stop key, an up key, a down key, a level adjust key, and an arterial pressure port. The display window displays the blood flow rate setting during blood pump operation. The start/stop key starts and stops the blood pump 132. The up and down keys increase and decrease the speed of the blood pump 132. The level adjust key raises a level of fluid in a drip chamber.

The hemodialysis machine 102 further includes a dialysate circuit formed by the dialyzer 110, various other dialysate components, and dialysate lines connected to the hemodialysis machine 102. Many of these dialysate components and dialysate lines are inside the housing 103 of the hemodialysis machine 102 and are thus not visible in FIG. 1. During treatment, while the blood pump 132 circulates blood through the blood circuit, dialysate pumps (not shown) circulate dialysate through the dialysate circuit.

A drain line 128 and an ultrafiltration line 129 extend from the hemodialysis machine 102. The drain line 128 and the ultrafiltration line 129 are fluidly connected to the various dialysate components and dialysate lines inside the housing 103 of the hemodialysis machine 102 that form part of the dialysate circuit. During hemodialysis, the dialysate supply line carries fresh dialysate to the portion of the dialysate circuit located inside the hemodialysis machine 102. As noted above, the fresh dialysate is circulated through various dialysate lines and dialysate components, including the dialyzer 110, that form the dialysate circuit. As the dialysate passes through the dialyzer 110, it collects toxins from the patient's blood. The resulting spent dialysate is carried from the dialysate circuit to a drain via the drain line 128. When ultrafiltration is performed during treatment, a combination of spent dialysate (described below) and excess fluid drawn from the patient is carried to the drain via the ultrafiltration line 129.

The dialyzer 110 serves as a filter for the patient's blood. The dialysate passes through the dialyzer 110 along with the blood, as described above. A semi-permeable structure (e.g., a semi-permeable membrane and/or semi-permeable microtubes) within the dialyzer 110 separates blood and dialysate passing through the dialyzer 110. This arrangement allows the dialysate to collect toxins from the patient's blood. The filtered blood exiting the dialyzer 110 is returned to the patient. The dialysate exiting the dialyzer 110 includes toxins removed from the blood and is commonly referred to as "spent dialysate." The spent dialysate is routed from the dialyzer 110 to a drain.

A drug pump 192 also extends from the front of the hemodialysis machine 102. The drug pump 192 is a syringe pump that includes a clamping mechanism configured to retain a syringe 178 of the blood component set 104. The drug pump 192 also includes a stepper motor configured to move the plunger of the syringe 178 along the axis of the syringe 178. A shaft of the stepper motor is secured to the plunger in a manner such that when the stepper motor is operated in a first direction, the shaft forces the plunger into the syringe, and when operated in a second direction, the shaft pulls the plunger out of the syringe 178. The drug pump 192 can thus be used to inject a liquid drug (e.g., heparin) from the syringe 178 into the blood circuit via a drug delivery line 174 during use, or to draw liquid from the blood circuit into the syringe 178 via the drug delivery line 174 during use.

The hemodialysis machine 102 includes a user interface with input devices such as a touch screen 118 and a control panel 120. The touch screen 118 and the control panel 120 allow the operator to input various different treatment parameters to the hemodialysis machine 102 and to otherwise control the hemodialysis machine 102. The touch screen 118 displays information to the operator of the hemodialysis system 100.

The hemodialysis machine 102 also includes a control unit 101 (e.g., a processor) configured to receive signals from and transmit signals to the touch screen 118 and the control panel 120. The control unit 101 can control the operating parameters of the hemodialysis machine 102, for example, based at least in part on the signals received by the touch screen 118 and the control panel 120. The hemodialysis machine 102 may also include a communication unit 105 that may be provided for wireless communication with a remote control device and may be communicatively coupled with the control unit 101.

Although discussed herein principally in connection with a particular configuration of hemodialysis machine, the system described herein may be used and implemented in connection with other configurations or types of hemodialysis machines and other medical devices, including peritoneal dialysis machines, and especially home medical devices, that would benefit from having a sterile work surface and/or platform door.

Figure 2:
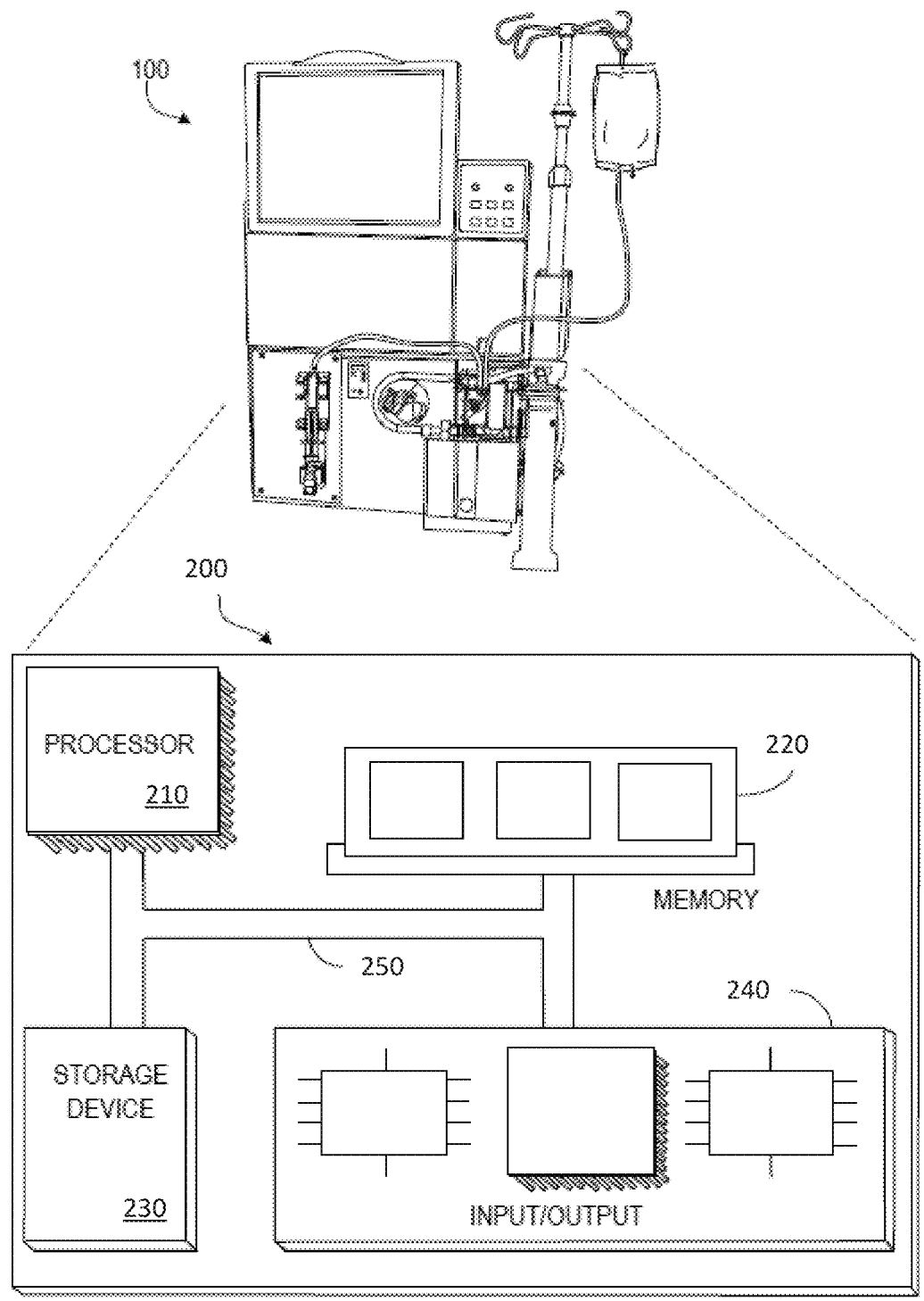
FIG. 2 is a schematic illustration of an example computer system illustrated in connection with the dialysis machine.

FIG. 2 is a block diagram of an example computer system 200 illustrated in connection with the dialysis machine 100. For example, the control unit 101 discussed above could be an example of the system 200 described here. The system 200 includes a processor 210, a memory 220, a storage device 230, and an input/output device 240. Each of the components 210, 220, 230, and 240 can be interconnected, for example, using a system bus 250. The processor 210 is capable of processing instructions for execution within the system 200. The processor 210 can be a single-threaded processor, a multi-threaded processor, and/or other computer. The processor 210 is capable of processing instructions stored in the memory 220 or on the storage device 230.

The memory 220 stores information within the system 200. In some implementations, the memory 220 is a computer-readable medium. The memory 220 can, for example, be a volatile memory unit or a non-volatile memory unit.

The storage device 230 is capable of providing mass storage for the system 200. In some implementations, the storage device 230 is a non-transitory computer-readable medium. The storage device 230 can include, for example, a hard disk device, an optical disk device, a solid-state drive, a flash drive, magnetic tape, or some other large capacity storage device. The storage device 230 may alternatively be a cloud storage device, e.g., a logical storage device including multiple physical storage devices distributed on a network and accessed using a network. In some implementations, the information stored on the memory 220 can also or instead be stored on the storage device 230.

The input/output device 240 provides input/output operations for the system 200. In some implementations, the input/output device 240 includes one or more of network interface devices (e.g., an Ethernet card), a serial communication device (e.g., an RS-232 10 port), and/or a wireless interface device (e.g., a short-range wireless communication device, an 802.11 card, a wireless modem (3G, 4G, 5G)). In some implementations, the input/output device 240 includes driver devices configured to receive input data and send output data to other input/output devices, e.g., a keyboard, a printer, and display devices (such as the touch screen display 118). In some implementations, mobile computing devices, mobile communication devices, and other devices are used. The input/output device 240 may further include the communication component 105 that is discussed in more detail elsewhere herein.

In some implementations, the computer system 200 is a microcontroller. A microcontroller is a device that contains multiple elements of a computer system in a single electronics package. For example, the single electronics package could contain the processor 210, the memory 220, the storage device 230, and input/output devices 240.

Figure 3:
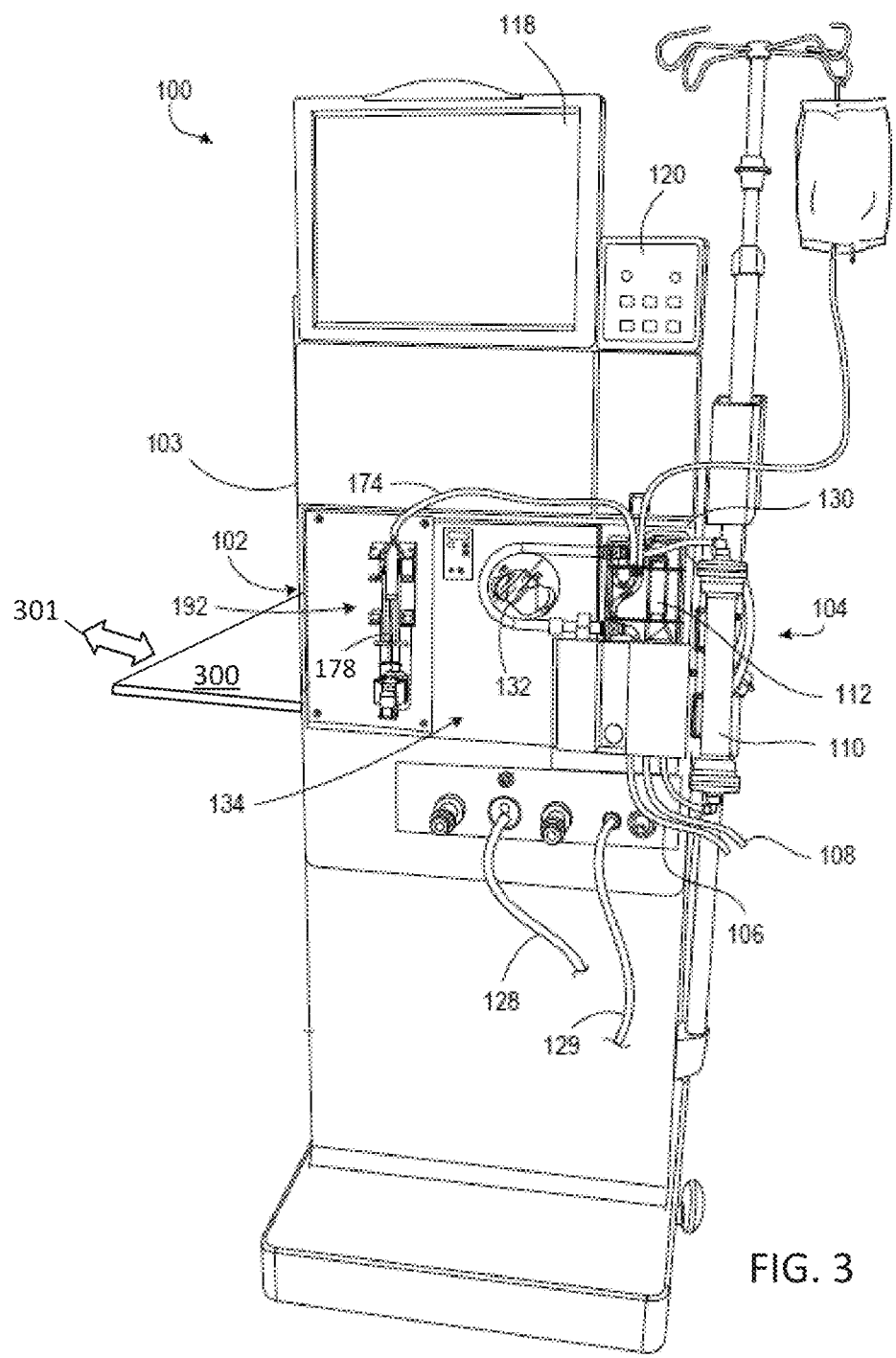
FIG. 3 is an illustration of the dialysis machine having an integrated work platform according to an exemplary embodiment of the system described herein.

FIG. 3 is an illustration of the dialysis machine 102 having an integrated sterile work platform 300 according to an exemplary embodiment of the system described herein. The platform 300 is shown in an open and extended position in which it is ready to be used as a platform on which tubing or other related dialysis treatment components may be placed until needed or installed on the dialysis machine 102. The arrow 301 indicates the direction of movement of the platform 300 in which the platform 300 may slide horizontally into, or out of, an internal port within the dialysis machine 102. The surface of the platform 300 may be disinfected or sterilized by one or more devices according to an implementation of the system described herein and further described in detail below. In an implementation, after sterilization, a sterile surface of the platform may be appropriate to maintain aseptic technique protocols, and thereby minimize contamination by pathogens, for tubing and dialysis components when the tubing and components are placed on the sterile surface of the platform 300.

Figure 4:
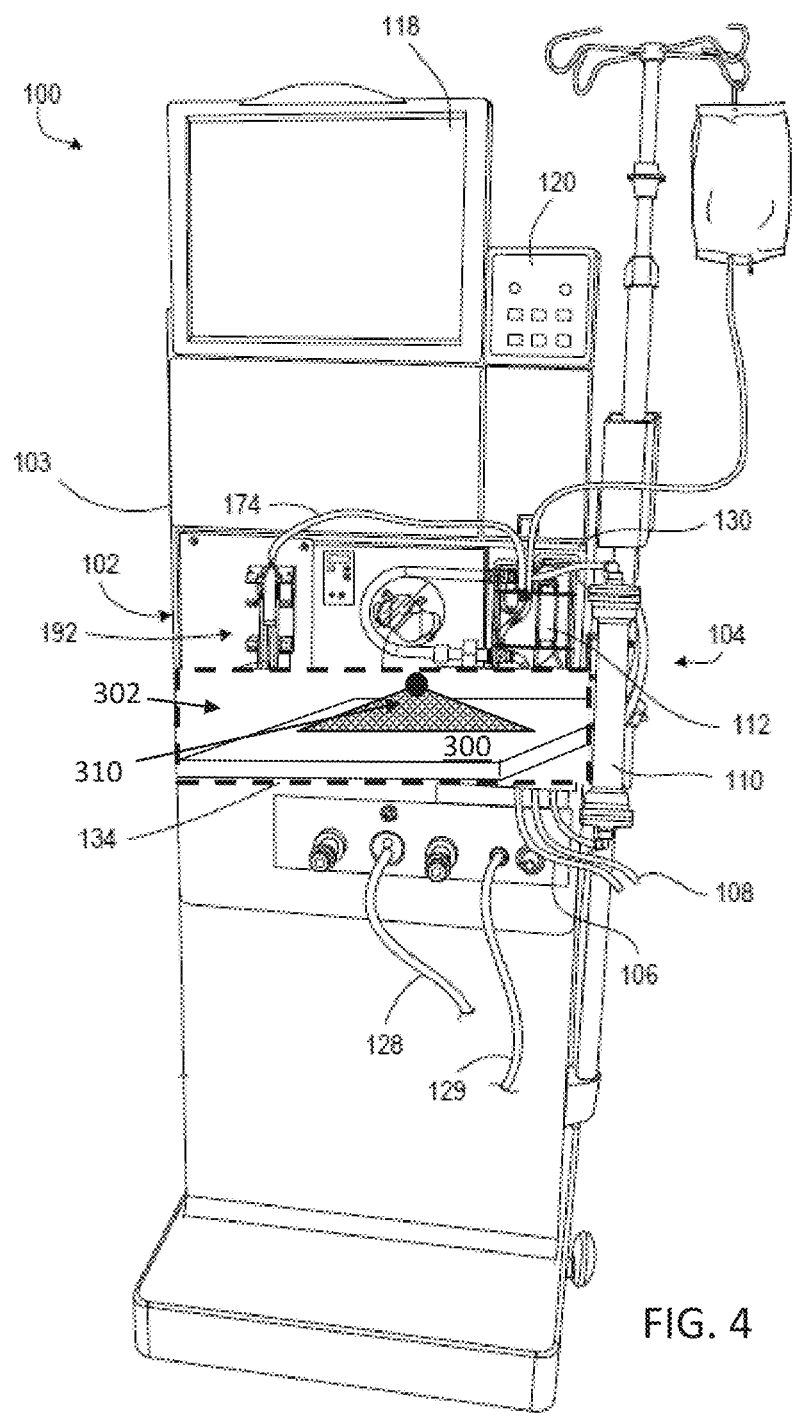
FIG. 4 is a schematic illustration showing the platform stowed in an internal port of the dialysis machine and including a UV light sterilization device according to an implementation of the system described herein.

FIG. 4 is a schematic illustration showing the platform 300 stowed in an internal port 302 of the dialysis machine 102 and including a sterilization device that is illustrated as an ultraviolet (UV) sterilization device 310 according to an implementation of the system described herein. In the illustrated embodiment, the UV sterilization device 310 may include a UV light source located in the internal port 302 of the dialysis machine 102 and is used to sterilize the platform 300 when the platform 300 is retracted into and/or otherwise stowed in the internal port 302.

Figure 5:
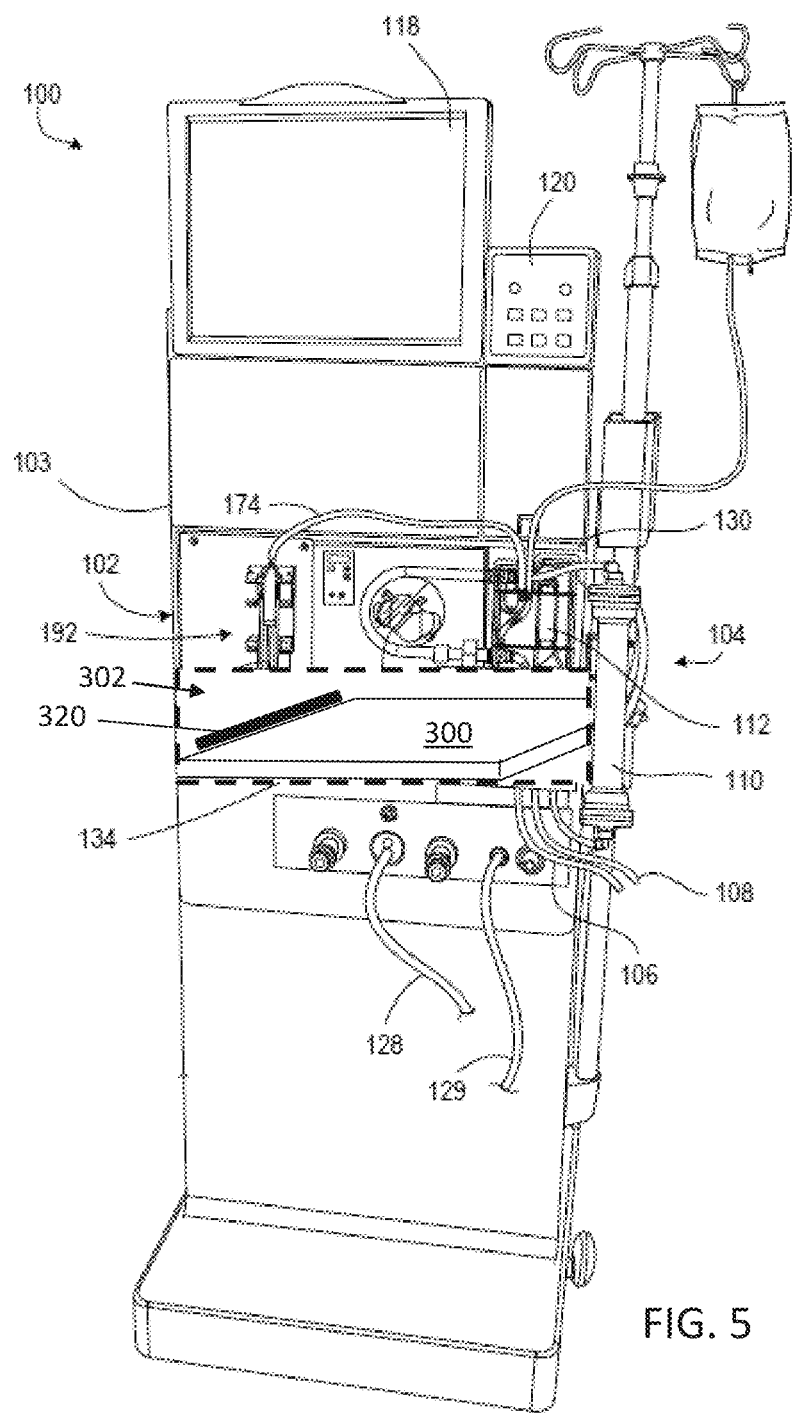
FIG. 5 is a schematic illustration showing the platform stowed in the internal port of the dialysis machine and including a disinfectant roller device for sterilizing the platform according to another implementation of the system described herein.

FIG. 5 is an illustration showing the platform 300 retracted into the internal port 302 of the dialysis machine 102 and including a disinfectant roller device 320 for sterilizing the platform 300 according to another implementation of the system described herein. In the illustrated embodiment, the disinfectant roller device 320 may include disinfectant rollers which sterilize the platform in connection with actions of retraction or extension of the platform 300 into and out of the internal port 302 of the dialysis machine 102. The disinfectant rollers may be covered with an appropriate chemical disinfectant that is applied to the surface of the platform 300 to perform the sterilization and may be replaceable, for example, periodically as part of maintenance procedures on the dialysis machine 102.

Figure 6A:
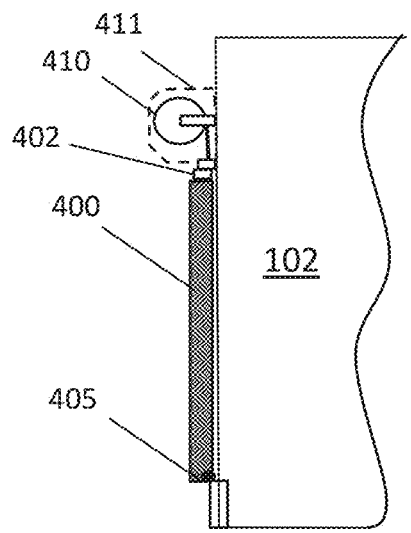
FIGS. 6A-6C are illustrations showing functioning of another example of an integrated sterile work platform for a dialysis machine according to another implementation of the described herein.
Figure 6B:
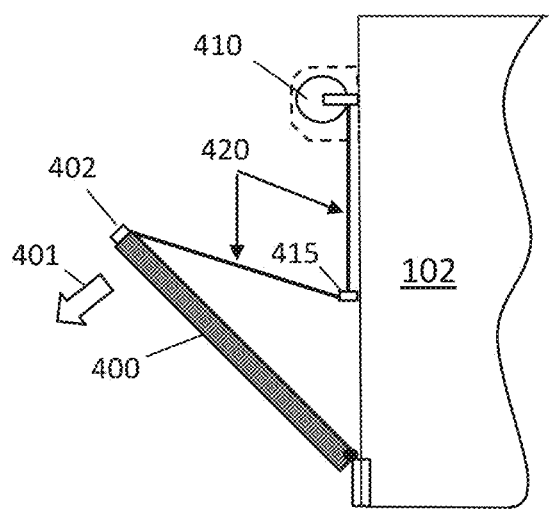
Figure 6C:
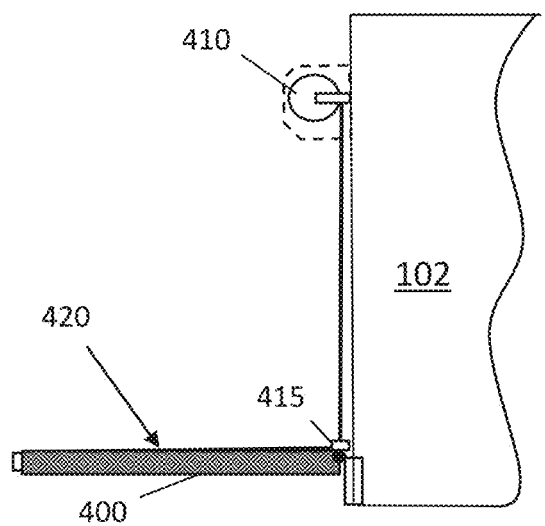

FIGS. 6A-6C are illustrations showing functioning of another example of an integrated sterile work platform 400 for a dialysis machine according to another implementation of the described herein. As shown in FIG. 6A, a dialysis machine, like the dialysis machine 102, may include the platform 400 that is hinged via a mechanism 405 or otherwise configured to be foldable from a substantially vertical position against the side of the dialysis machine 102 to a substantially horizontal work position. The platform 400 may be manually opened and closed, or, alternatively, may be automatically extended and retracted, e.g., for which the mechanism 405 has a motor and/or other drive components. In the figure, the platform 400 is shown in its retracted, folded position against the side of the dialysis machine 102. A roll 410 of sterile material, e.g. paper or plastic, may be disposed under a protective cover 411 on the side of the dialysis machine 102. The material from the roll 410 may extend to the end of the platform 400 and be held in place by a clamp 402 at the end of the platform 400.

FIG. 6B shows that when the platform 400 is to be used, the platform 400 may be folded away from the vertical position, shown by arrow 401. As that folding action occurs, the sterile material 420, held in place by the clamp at the end of the platform 400, is unwound or otherwise dispensed from the roll 410 to the surface of the platform 400. A sliding guide 415 may be used to ensure the sterile material 420 dispenses properly from the roll 410.

FIG. 6C shows the platform 400 in its fully open and usable position and for which the sterile material 420 covers the surface of the platform 400. The sliding guide 415 is shown in its fully extended position at the base of the platform 400. The platform 400 is thereby usable to support tubing or other components in a sterile manner by virtue of the sterile material 420 covering the surface of the platform 400. After use, the sliding guide may be returned its initial position, the clamp 402 released, and the used sterile material 420 removed. Thereafter, a new end of the sterile material protruding from the sliding guide 415 may be attached to the end of the platform 400, using the clamp 402, after the platform has been folded back into its retracted position against the side of the dialysis machine 102.

Depending on machine type and configuration, a dialysis machine may include front panel doors that act as a safeguard to protect dialysis machine components when the machine is not in use and, during use, to prevent an operator from encountering a pinch hazard of rotating blood pumps during the treatment. In such case, the doors may be opened only before and after the dialysis treatment. The doors may be transparent so the operator may visually check the connections during the treatment. After each treatment, the doors, along with the other surfaces of the dialysis machine, are disinfected.

Figure 7:
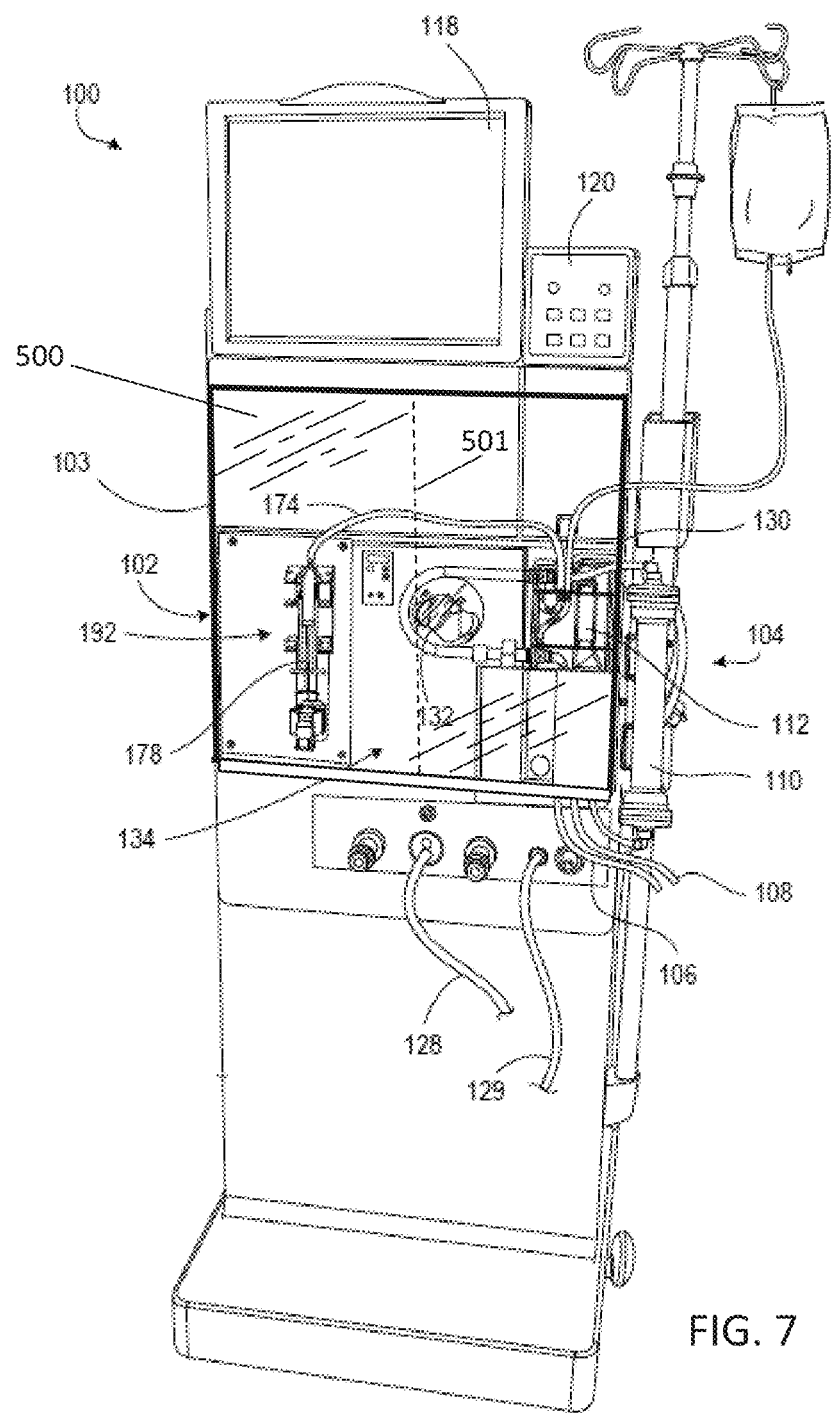
FIG. 7 is an illustration of another example of an integrated work platform according to another implementation of the system described herein.

FIG. 7 is an illustration of another example of an integrated work platform 500 according to another implementation of the system described herein. In this example, the platform 500 may have multiple configurations and serve multiple functions on the dialysis machine 102. Specifically, the platform 500 may be configured and disposed to act as a vertical door when the platform 500 is in a folded or retracted position and as a horizontal work surface when the platform 500 is an open and extended position. In this figure, the platform 500 is shown folded against the front of the dialysis machine 500 and may be transparent such that an operator can see through the platform 500 to the components of the dialysis machine covered by the platform 500. In an implementation, the platform 500 may be a single surface that is extended by folding the surface downward to form a work surface platform, as further discussed below. Alternatively, as shown schematically by dashed line 501, the surface 500 may have multiple parts that are configured to open sideways like dual door panels when an operator opens the door to access the dialysis machine, and which surfaces may be further configured to be locked together and then hinged to collectively fold downward to form the work platform, when such horizontal platform is desired.

Figure 8:
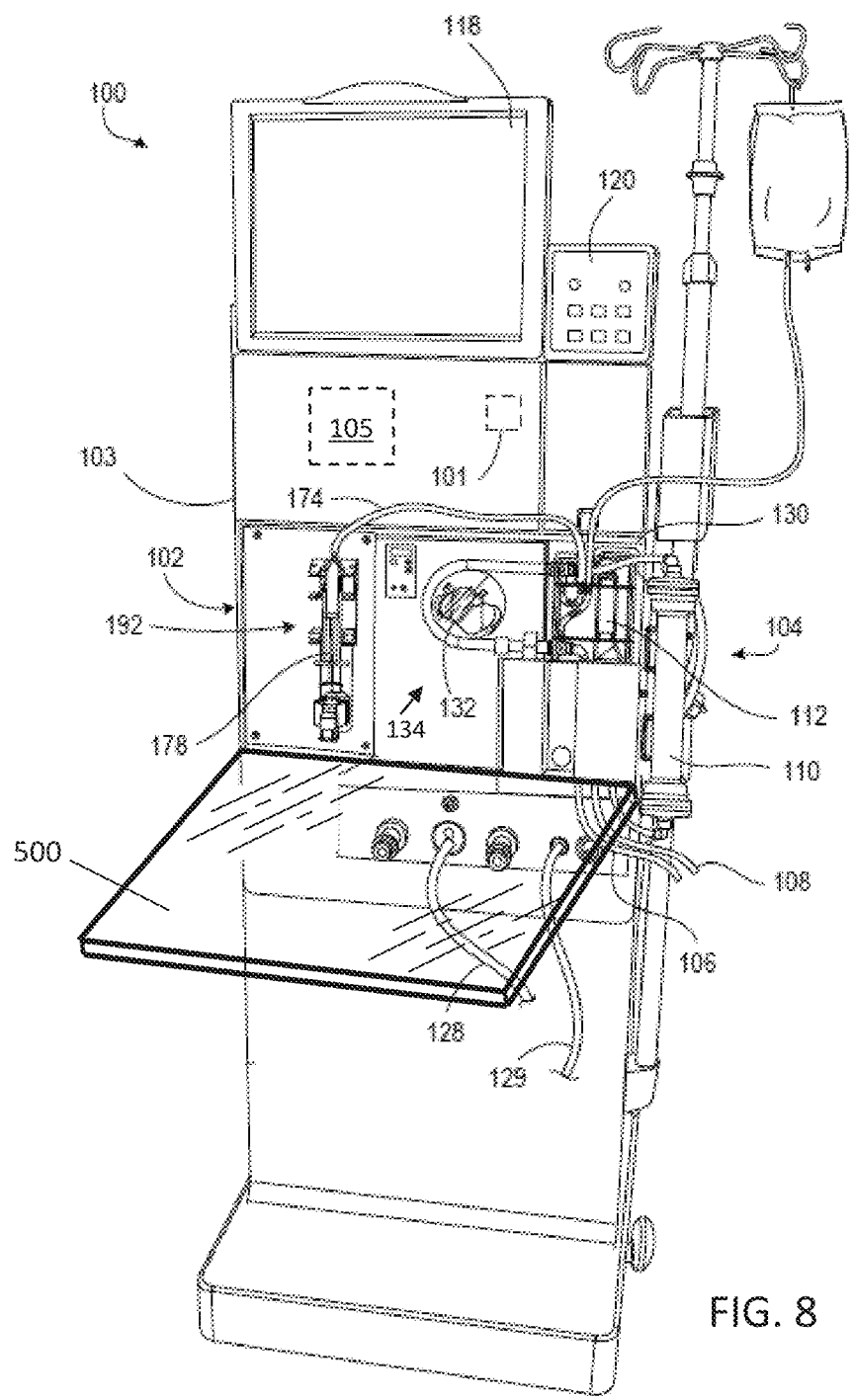
FIG. 8 is an illustration showing the work platform in an open, horizontal and useable position for supporting tubing or other components placed thereon according to an implementation of the system described herein.

FIG. 8 is an illustration showing the work platform 500 in an open, horizontal and useable position for supporting tubing or other components placed thereon according to an implementation of the system described herein. The surface of the platform 500 that is moved from the vertical door position to the horizontal work platform position may be expected to be sterile in accordance with cleaning and disinfection protocols that would have occurred following a prior treatment performed with the dialysis machine 102. The sterile nature of the surface of the platform 500 would be preserved in the closed vertical position by facing inward to the dialysis machine 102. Accordingly, in the illustrated open, horizontal position, the platform 500 may be used for conveniently laying tubing and other dialysis treatment components prior to installing the tubing and components for the next dialysis treatment, and while reducing risk of contamination that might otherwise occur were the tubing and components placed elsewhere on a non-sterile surface.

Figure 9:
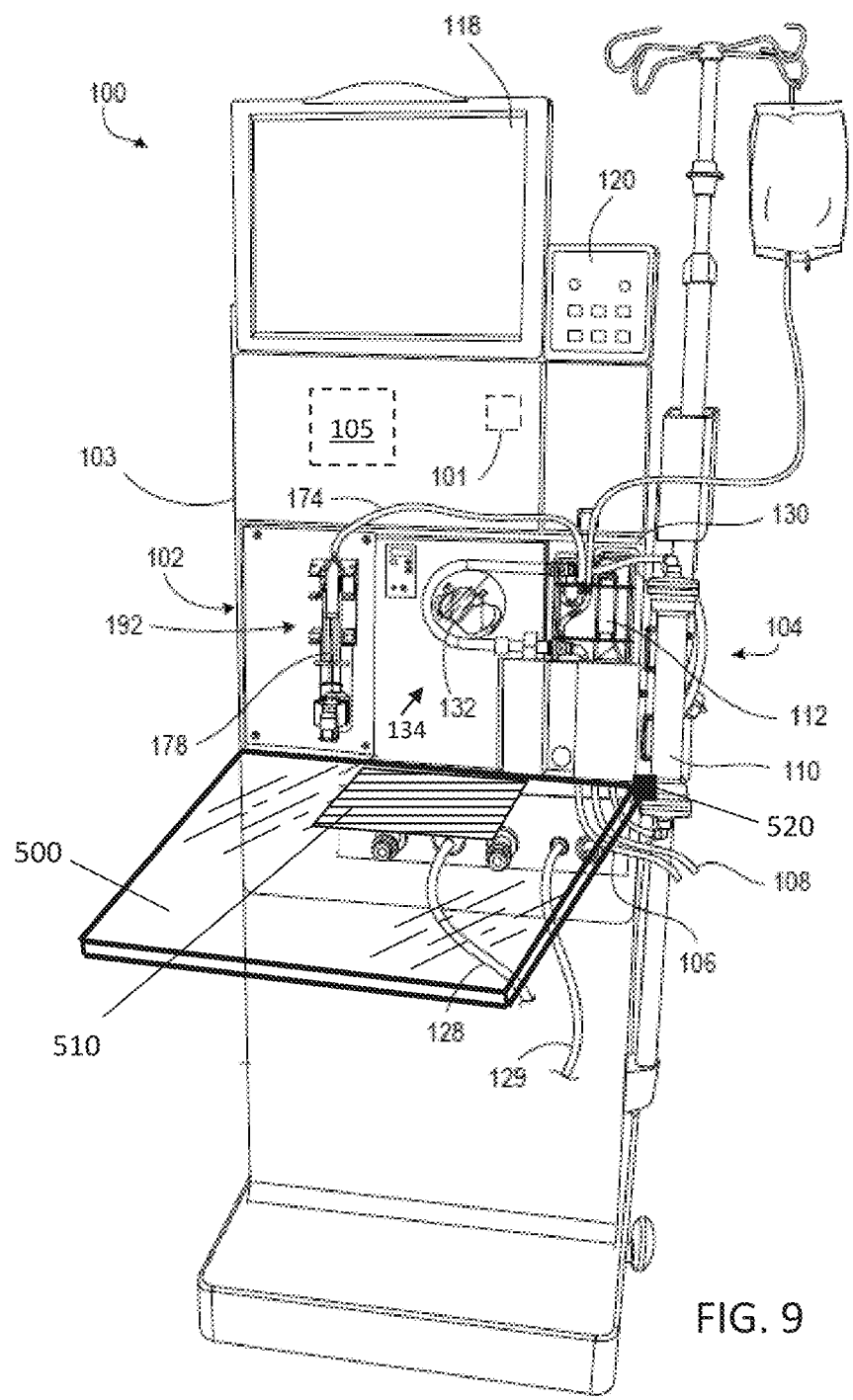
FIG. 9 is an illustration showing an information screen incorporated into the work platform according to another implementation of the system described herein.

FIG. 9 is an illustration showing an information screen 510 incorporated into the work platform 500 according to an implementation of the system described herein. In order to better facilitate checking the myriad points on the extracorporeal blood circuit during setup, a checklist, e.g. a digital checklist, may be displayed on the information screen 510 of the work platform 500. To prevent the letters or diagram of the checklist on the information screen 510 from obstructing the view through the transparent door when it is in the closed position during treatment, an electrically controlled opacity technology, such as, e.g., a Smart Tint® product and/or other smart glass technology, may be used.

In some implementations, a sensor 520 indicates the position of the work platform 500, such as whether the platform 500 is in the vertical door position or the horizontal work platform position. In some implementations, the sensor may be an optical sensor and/or a mechanical switch based sensor. When the sensor 520 indicates the platform 500 is in the horizontal work platform position, an electric current from the dialysis machine 102, e.g. controlled using the control unit 101 (e.g. a processor), activates the opacity-controlled checklist/diagram on the information screen 510, showing the operator to which extracorporeal blood circuit features the operator should pay special attention. After the extracorporeal blood circuit has been checked and placed on the machine modules, the work platform 500 is raised up by the operator to the vertical door position, the opacity-controlled checklist is switched off, and the blood pump may start turning to load the blood pump tubing segments. In other implementations, information from remote sources or an external network may be displayed on the information screen 510, for example, via communication using the communication unit 105. The information screen 510 may digitally display instructions for installation of tubing and components and/or operation of the dialysis machine 102 and/or may display communications from a caregiver, doctor or clinician, and including display details of the treatment prescription to be performed by the dialysis machine 102.

Because the door itself is part of a dialysis machine, it is disinfected inside and outside at the end of every treatment by the operator in accordance with established protocols, with the inside of the door in particular being protected from surface contamination by being enclosed against the dialysis machine. Accordingly, under the established disinfecting protocols, the inside door surface/upward horizontal work platform surface is disinfected at the end of a treatment and then raised/closed into its secure position, thereby ensuring the interior/upward surface remains sterile the next time the platform 500 is opened or lowered.

Examples and implementations discussed herein may be combined with each other in appropriate combinations in connection with the system described herein. Additionally, in some instances, the order of steps in flow diagrams, flowcharts and/or described flow processing may be modified, where appropriate. The system may further include a display and/or other computer components for providing a suitable interface with a user and/or with other computers. Aspects of the system described herein may be implemented or controlled using software, hardware, a combination of software and hardware and/or other computer-implemented or computer-controlled modules or devices having described features and performing described functions.

Data exchange and/or signal transmissions to, from and between components of the system may be performed using wired or wireless communication. This communication may include use of one or more transmitter or receiver components that securely exchange information via a network, such as the Internet, and may include use of components of local area networks (LANs) or other smaller scale networks, such as Wi-Fi, Bluetooth or other short range transmission protocols, and/or components of wide area networks (WANs) or other larger scale networks, such as mobile telecommunication networks.

Software implementations of aspects of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media, a memory card, a flash drive or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system. The meanings of any method steps of the invention(s) described herein are intended to include any suitable method of causing one or more parties or entities to perform the steps unless a different meaning is expressly provided or otherwise clear from the context.

As used herein, an element or operation recited in the singular and preceded with the word "a" or "an" should be understood as not excluding plural elements or operations, unless such exclusion is explicitly recited. References to "one" embodiment or implementation of the present disclosure are not intended to be interpreted as excluding the existence of additional embodiments that also incorporate the recited features. Furthermore, a description or recitation in the general form of "at least one of [a], [b] or [c]," or similar, should be generally construed to include [a] alone, [b] alone, [c] alone, or any combination of [a], [b] and [c].

Other examples and implementations of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A medical device system, comprising:
    a medical device; and
    a platform moveably coupled to the medical device, wherein, in a first position, the platform is positioned within or against the medical device, and, in a second position, the platform is extended from the medical device and disposed in a horizontal position, wherein, after the platform is extended to the second position, a surface of the platform is sterile.

2. The medical device system of claim 1, further comprising a sterilization device coupled to the medical device that sterilizes the surface of the platform.

3. The medical device system of claim 2, wherein the sterilization device is disposed in an internal port of the medical device, and wherein the sterilization device sterilizes the surface of the platform after the platform is retracted into the internal port of the medical device.

4. The medical device system of claim 2, wherein the sterilization device includes an ultraviolet (UV) light sterilization device that exposes the surface of the platform to UV light.

5. The medical device system of claim 2, wherein the sterilization device includes at least one disinfectant roller that engages the surface of the platform.

6. The medical device system of claim 1, further comprising a sterile material assembly that applies a sterile material to the surface of the platform when the platform is moved from the first position to the second position.

7. The medical device system of claim 6, wherein the sterile material assembly includes a dispenser that dispenses the sterile material and a guide that guides the sterile material onto the surface of the platform.

8. The medical device system of claim 1, wherein, in the first position, the platform is a door to the medical device, and wherein the platform is made of a transparent material.

9. The medical device system of claim 1, wherein, in the second position, the platform includes an information screen that is formed into the surface of the platform and that presents information when the platform is in the second position.

10. The medical device system of claim 9, wherein the information screen is a digital screen.

11. The medical device system of claim 9, wherein the information screen is formed in the platform using electrically controlled opacity.

12. The medical device system of claim 9, further comprising a sensor that senses when the platform is in the first position and the second position, and wherein the information screen is removed when the platform is in the first position.

13. The medical device system of claim 9, further comprising a control unit of the medical device that controls display of the information screen on the platform.

14. The medical device system of claim 13, further comprising a communication unit that receives information from a remote source that is displayed on the information screen of the platform.

15. A dialysis system, comprising:
    a dialysis machine; and
    a platform moveably coupled to the dialysis machine, wherein, in a first position, the platform is positioned within or against the dialysis machine, and, in a second position, the platform is extended from the medical device and disposed in a horizontal position, wherein, after the platform is extended to the second position, a surface of the platform is sterile.

16. The dialysis system of claim 15, further comprising a sterilization device disposed in an internal port of the medical device that sterilizes the surface of the platform when the platform is in the first position.

17. The dialysis system of claim 16, wherein the sterilization device includes one or more of an ultraviolet light source or at least one disinfectant roller.

18. The dialysis system of claim 15, wherein the platform is made of a transparent material and includes an information screen integrated into the platform.

19. The dialysis system of claim 18, wherein the information screen is presented on the transparent material of the platform using electrically controlled opacity.

* * * * *